United States Patent
Matsui et al.

(10) Patent No.: US 10,712,332 B2
(45) Date of Patent: Jul. 14, 2020

(54) SOLUTION TANK DEVICE

(71) Applicant: HITACHI, LTD, Chiyoda-ku, Tokyo (JP)

(72) Inventors: Kazuma Matsui, Tokyo (JP); Itaru Yanagi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 259 days.

(21) Appl. No.: 15/755,389

(22) PCT Filed: Feb. 12, 2016

(86) PCT No.: PCT/JP2016/054141
§ 371 (c)(1),
(2) Date: Feb. 26, 2018

(87) PCT Pub. No.: WO2017/138149
PCT Pub. Date: Aug. 17, 2017

(65) Prior Publication Data
US 2018/0252696 A1  Sep. 6, 2018

(51) Int. Cl.
| G01N 33/487 | (2006.01) |
| B01L 3/00 | (2006.01) |
| B82Y 30/00 | (2011.01) |
| B82Y 5/00 | (2011.01) |
| C12Q 1/6869 | (2018.01) |

(52) U.S. Cl.
CPC .. *G01N 33/48721* (2013.01); *B01L 3/502746* (2013.01); *B01L 2300/0896* (2013.01); *B82Y 5/00* (2013.01); *B82Y 30/00* (2013.01); *C12Q 1/6869* (2013.01)

(58) Field of Classification Search
CPC ......... G01N 33/48721; G01N 27/3278; G01N 21/658; B01L 3/502746; B01L 2300/0896; B82Y 30/00; B82Y 5/00; B82Y 15/00; C12Q 1/6869; G01J 3/0267
See application file for complete search history.

(56) References Cited

U.S. PATENT DOCUMENTS

2013/0176563 A1   7/2013  Ozawa et al.
2014/0353509 A1   12/2014  Nakatsugawa

FOREIGN PATENT DOCUMENTS

| JP | 2005098790 A | 4/2005 |
| JP | 2005291846 A | 10/2005 |
| JP | 2008039584 A | 2/2008 |
| JP | 2015037409 A | 2/2015 |
| JP | 2015222261 A | 12/2015 |

OTHER PUBLICATIONS

Venta, K. et al. "Differentiation of Short Single-Stranded DNA Homopolymers in Solid-State Nanopores", ACS Nano. May 28, 2013; 7(5): pp. 4629-4636.

*Primary Examiner* — Lore R Jarrett
(74) *Attorney, Agent, or Firm* — Procopio, Cory, Hargreaves & Savitch LLP

(57) ABSTRACT

A solution tank device comprises: an insulating thin film, which is configured to allow an object to be measured to pass therethrough, and has a thickness of 1 micrometer or less; a first solution tank, which is configured to support one surface of both surfaces of the insulating thin film; and a first conductive structure, which has a sheet resistance of $10^{13}$ ohms or less in a portion in which contact friction occurs between the first solution tank and an object outside of the first solution tank.

16 Claims, 9 Drawing Sheets

SOLUTION TANK DEVICE

BACKGROUND

This invention relates to a structure for performing measurement through use of a thin film device.

A nanopore sequencer is a system configured to measure a current value of an object to be measured that passes through a nanopore embedded in a thin film. For example, when the object to be measured is deoxyribonucleic acid (DNA), and the DNA passes through the nanopore, a current value for sealing the nanopore (hereinafter referred to as "sealing current value") varies depending on a difference in base (adenine (A), guanine (G), cytosine (C), or thymine (T)) forming the DNA. With this, the nanopore sequencer can identify a base sequence.

As factors for determining DNA reading accuracy of the nanopore sequencer, there are given, for example, the thickness of a thin film in which a nanopore is formed, and the magnitude of noise of a current that passes through the nanopore. It is preferred that the thickness of the thin film be small. Each interval between adjacent bases of four kinds of bases arranged in a DNA strand is about 0.34 nanometer. As the thickness of the thin film becomes larger as compared to the interval, a larger number of bases simultaneously enter the nanopore, and hence a signal obtained as a sealing current is a signal derived from a plurality of bases. Therefore, the determination accuracy of a base sequence is deteriorated, and signal analysis also becomes more complicated. It is also preferred that a noise current be smaller. The noise current is added to a value of the sealing current. In order to increase an identification rate of the four kinds of bases, it is required that the sealing current be reduced.

In a document of Venta (Venta, K., et al., Differentiation of Short, Single-Stranded DNA Homopolymers in Solid-State Nanopores, ACS Nano 7(5), pp. 4629-4636 (2013)), it is disclosed that a difference in sealing current derived from base kinds at a time when the DNA passes through the nanopore of the thin film is observed. In this document of Venta, in order to increase an identification rate of the sealing current, a nanopore is formed in a SiN membrane of a thin film, and an insulating film is applied thereto. With this, a device capacitance is decreased to reduce a noise current.

A thin film for biological polymer measurement has a problem in that the thin film is liable to be influenced by a potential difference between solutions on both sides of the thin film and breaks due to the potential difference. In particular, when the device capacitance is decreased in order to reduce the noise current, the probability that an initial defect occurs in the thin film increases.

It was verified by an experiment that the noise current was able to be reduced by applying an insulating film to a device including a thin film membrane having a thickness of from 12 nanometers to 20 nanometers to decrease the device capacitance. Meanwhile, it was verified that, when solutions were filled in chambers on both surface sides of the thin film of a low-capacitance device having reduced noise, an initial defect in which the thin film broke occurred in most cases. This initial defect is not referred to in the document of Venta. Therefore, the mechanism of the initial defect and the countermeasures against the initial defect remain unknown.

As a result of the investigation, it was found that the initial defect occurred when a potential difference $\Delta V(=\Delta Q/C)$ applied to the thin film increased along with decrease in device capacitance C depending on a charge difference $\Delta Q$ of the solutions filled on both sides of the thin film, to thereby subject the thin film to dielectric breakdown. Further, it was found that one of major factors of the occurrence of the charge difference was static electricity generated on an outer side of a solution tank in which the solution was filled.

The static electricity is generated when substances approach each other up to about several nanometers or less and are charged by contact friction. It has been known that, when two kinds of substances are charged by contact friction, the charge amount thereof varies depending on the substance. In a method using a substance formed of the same material as that for a substance to be subjected to contact friction or a substance close to the substance to be subjected to contact friction in triboelectric series, a partner substance to be subjected to contact friction is limited. Thus, there is a risk in that the substance is charged through a change in atmospheric condition or contact friction with another substance. Further, countermeasures for adjusting the atmospheric condition, such as accelerating discharge by raising humidity or using an ionizer, require maintenance of equipment for adjusting the atmospheric condition. Further, there is a problem of noise caused by vibration of the equipment for adjusting the atmospheric condition.

SUMMARY

This invention provides a structure for suppressing an initial defect of a thin film.

An aspect of the invention disclosed in this application is a solution tank device, comprising: an insulating thin film, which is configured to allow an object to be measured to pass therethrough, and has a thickness of 1 micrometer or less; a first solution tank, which is configured to support one surface of both surfaces of the insulating thin film; and a first conductive structure, which has a sheet resistance of $10^{13}$ ohms or less in a portion in which contact friction occurs between the first solution tank and an object outside of the first solution tank.

According to the representative embodiment of this invention, a probability of breakage of the thin film caused by the potential difference between the solutions can be reduced. Other objects, configurations, and effects than those described above are clarified by the following description of an embodiment.

DETAILED DESCRIPTION OF THE EMBODIMENT

First Embodiment

First, based on experimental results, description is given of an effect of reducing a noise current in association with decrease in device capacitance, principle for occurrence of an initial defect at a time when solutions are filled on both surface sides of a thin film following the decrease in device capacitance, and a mechanism of preventing the initial defect.

<Thin Film Device>

Figure 1:
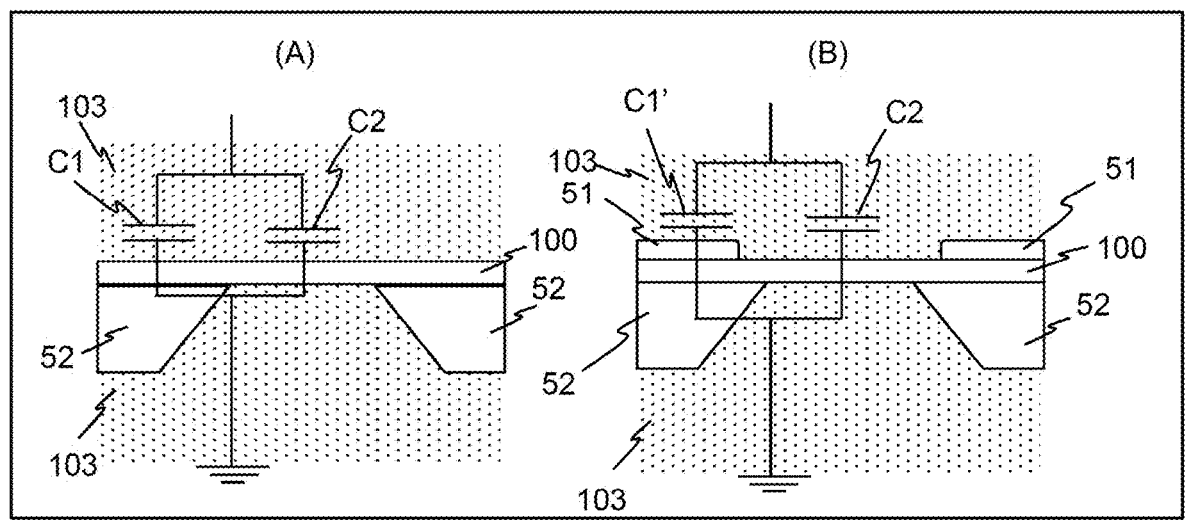
FIG. 1 is a sectional view of a thin film device.

FIG. 1 is a sectional view of a thin film device. (A) of FIG. 1 is a sectional view of the thin film device having no insulating film 51 applied thereto, and (B) of FIG. 1 is a sectional view of the thin film device having the insulating film 51 applied thereto. The thin film device includes a thin film 100 and a support substrate 52 configured to support the thin film 100. A front surface side (upper side in (A) and (B)) and a back surface side (lower side in (A) and (B)) of the thin film 100 are filled with a solution 103. The solution 103 and the thin film device are sealed in solution tanks (not shown). The thin film 100 is, for example, a SiN thin film having a thickness of 20 nanometers and an area of 100 square micrometers or less. The support substrate 52 is, for example, a silicon substrate having a thickness of 725 micrometers.

In (A), a first capacitance of a region on a side on which the support substrate 52 is present is represented by C1, and a second capacitance of a region on a side on which the support substrate 52 is not present is represented by C2. A combined capacitance C of the thin film device is C=C1+C2. In (B), the insulating film 51 is applied to a surface of the thin film 100 on an opposite side of the back surface supported by the support substrate 52. A first capacitance of a region on a side on which the support substrate 52 is present is represented by C1', and a second capacitance of a region on a side on which the support substrate 52 is not present is represented by C2. A combined capacitance C' is C'=C1'+C2.

The insulating film 51 is applied to the thin film device of (B) of FIG. 1, and hence the first capacitance C1' of the thin film device of (B) of FIG. 1 is lower than the first capacitance C1 of the thin film device of (A) of FIG. 1 (C1>C1'). Thus, the combined capacitance C' of the thin film device of (B) of FIG. 1 is lower than the combined capacitance C of the thin film device of (A) of FIG. 1 (C>C').

Figure 2:
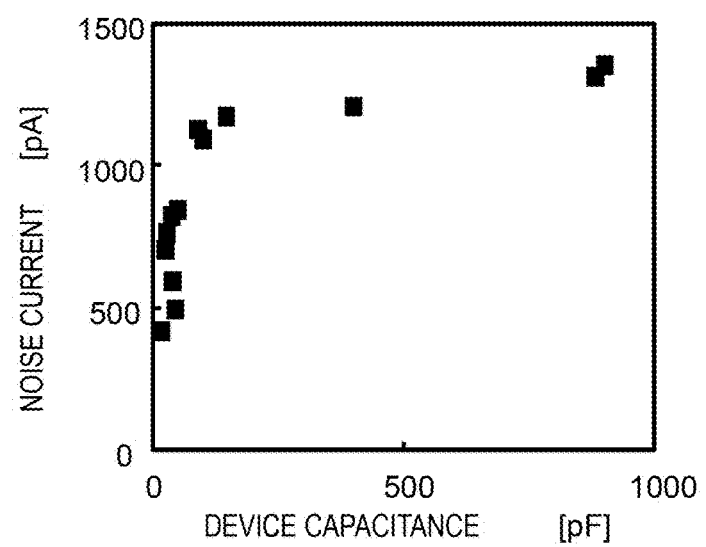
FIG. 2 is a graph for showing a relationship between a device capacitance and a noise current.

FIG. 2 is a graph for showing a relationship between a device capacitance and a noise current. The horizontal axis represents the device capacitance (combined capacitance of the thin film device), and the vertical axis represents the noise current. It was verified that, when an application amount of the insulating film 51 was increased in (B) of FIG. 1, the noise current was able to be reduced through reduction of the combined capacitance C'. As a result, in the same manner as in the document of Venta, the noise current was monotonously reduced along with decrease in device capacitance also in the thin film device manufactured by the inventors of this invention. As described above, reduction of noise through application of the insulating film 51 was verified. Meanwhile, it was found that the initial defect occurred following the decrease in device capacitance when the solution 103 was filled in the chambers on both the surface sides of the thin film 100 of the low-capacitance device having reduced noise as described above.

Figure 3:
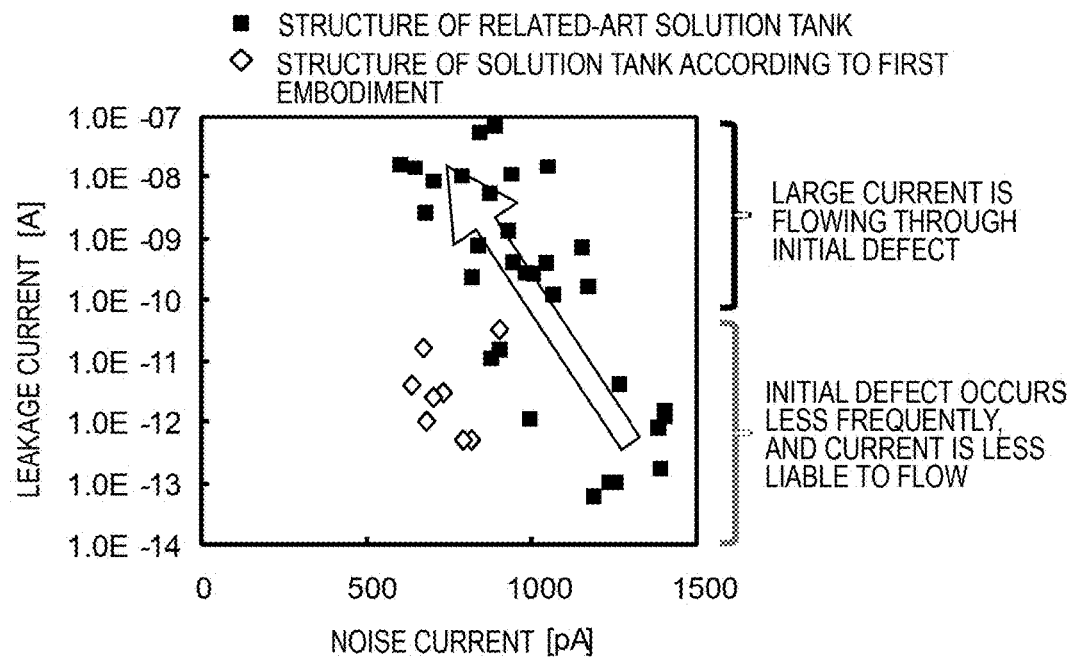
FIG. 3 is a graph for showing a relationship between a noise current and a leakage current.

FIG. 3 is a graph for showing a relationship between a noise current and a leakage current. The horizontal axis represents the noise current, and the vertical axis represents the leakage current. In the graph of FIG. 3, there are shown experimental results of the presence or absence of occurrence of the initial defect, which are obtained by comparing the noise current and the leakage current to each other, with the bandwidth of the noise current being 1 megahertz and the applied voltage of the leakage current being 0.1 volt.

In this experiment, when the thin film 100 is not broken or when a small defect having a size of about 1 nanometer occurs in the thin film 100, a value of a current flowing at a time when a voltage of 0.1 volt is applied is about $10^{10}$ amperes or less. Meanwhile, when the initial defect having a size of 1 nanometer or more occurs in the thin film 100, a current of about $10^{10}$ amperes or more flows through the initial defect at a time of application of the voltage of 0.1 volt.

As shown in FIG. 3, as a solution tank device has a smaller noise current, the capacitance of the solution tank device is decreased. In a related-art solution tank device including only an insulating material, a leakage current increases along with reduction in noise current. Meanwhile, in the solution tank device according to a first embodiment of this invention, a conductive material is applied to an outside of a solution tank formed of an insulating material as described later. Thus, as compared to the related-art solution tank device, the leakage current is significantly reduced to suppress occurrence of the initial defect.

<Occurrence Mechanism of Initial Defect>

Figure 4:
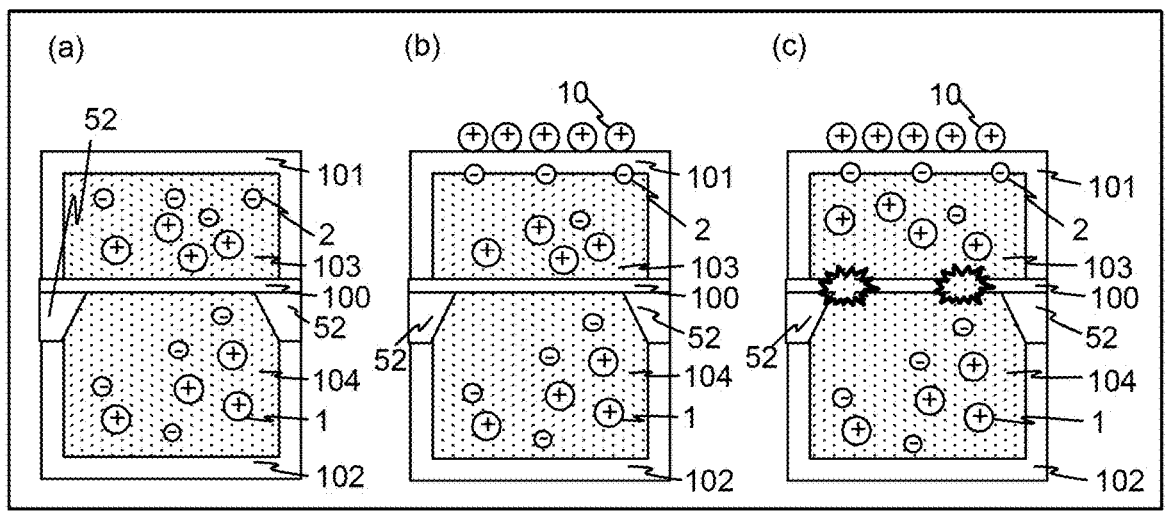
FIG. 4 is an explanatory view for illustrating a mechanism in which the initial defect is caused by static electricity generated outside of solution tanks.

FIG. 4 is an explanatory view for illustrating a mechanism in which the initial defect is caused by static electricity generated outside of solution tanks. (a) of FIG. 4 corresponds to an initial state. (b) of FIG. 4 corresponds to a state subsequent to the initial state of (a) of FIG. 4. (c) of FIG. 4 corresponds to a state subsequent to the state of (b) of FIG. 4. In the initial state of (a) of FIG. 4, it is assumed that there is no static electricity 10 outside of solution tanks 101 and 102 forming the solution tank device, and there is no difference between the amount of charge contained in the solution 103 and the amount of charge contained in a solution 104. In the state of (b) of FIG. 4, when it is assumed that the static electricity 10 is generated outside of the solution tank 101, the static electricity 10 generated outside of the solution tank 101 and the charge contained in the solution 103 in the solution tank 101 form an electric double layer. When it is assumed that the static electricity 10 generated outside of the solution tank 101 has positive charge, the charge contained in the solution 103 forming the electric double layer is negative charge, and a diffusion layer of the solution 103 and the charge of a bulk solution are biased to a positive side.

When the amount of the static electricity 10 of the solution tank 101 on the upper side and the amount of the static electricity 10 of the solution tank 102 on the lower side are different from each other, a difference is caused between charge amounts Q1 and Q2 of the solutions 103 and solutions 104. A charge difference $\Delta Q=|Q1-Q2|$ between the solutions 103 and 104 gives a potential difference $\Delta V(=\Delta Q|C)$ to the thin film 100. In particular, when the capacitance C of the thin film device is small, the potential difference $\Delta V$ increases, and the thin film 100 is subjected to dielectric breakdown to form pores as illustrated in the state of (c) of FIG. 4.

Figure 5:
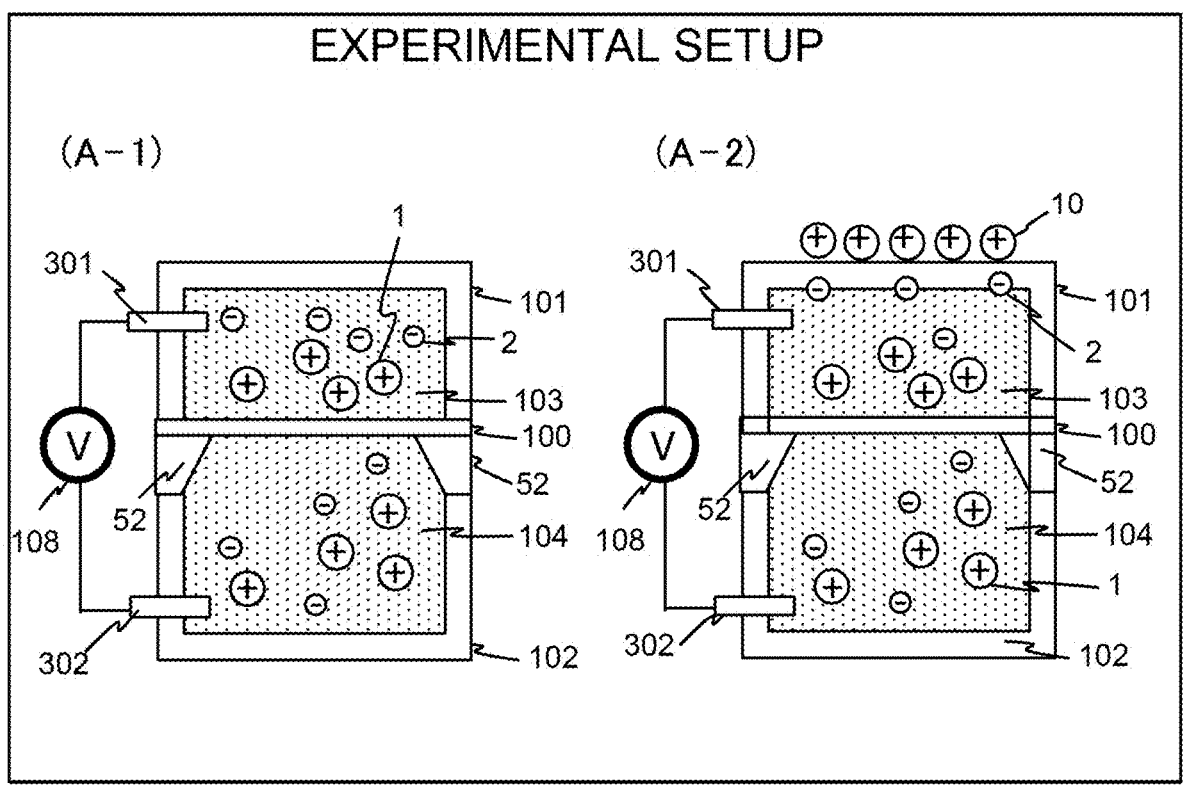
FIG. 5 is an explanatory view for illustrating an experimental setup.

FIG. 5 is an explanatory view for illustrating an experimental setup. The experimental setup is an experimental apparatus configured to give a potential difference for subjecting the thin film 100 to dielectric breakdown through generation of the static electricity 10. In this experiment, a thin film device having a high capacitance of 1,000 picofarads was used so that the thin film 100 was not broken due to the charge difference caused by the static electricity 10.

An initial state of this experiment is set to a state in which a charge difference is eliminated between the solutions 103 and 104 as illustrated in part (A-1) of FIG. 5, and in which the static electricity 10 is applied to an outside of the solution tank 101 by contact friction with respect to an external object as illustrated in part (A-2) of FIG. 5. The external object is, for example, a surface on which the solution tank device is installed, a jig configured to hold the solution tanks, or the hand of a user.

Figure 6:
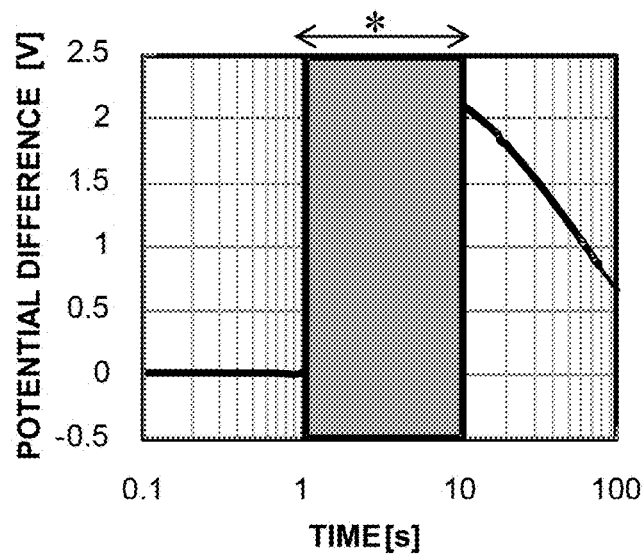
FIG. 6 is a graph for showing a change with the passage of time in potential difference between both the surface sides of the thin film having the static electricity applied thereto.

FIG. 6 is a graph for showing a change with the passage of time in potential difference between both the surface sides of the thin film 100 having the static electricity 10 applied thereto. The horizontal axis of the graph represents time, and the vertical axis thereof represents a potential difference between both the surface sides of the thin film 100. In the graph, time during which the static electricity 10 is applied is represented by a symbol "*". After the static electricity 10 is applied, the potential difference increases to 2 volts. It is considered that this potential difference further increases when the device capacitance is decreased. For example, when SiN having a capacitance of 100 picofarads and a thickness of 10 nanometers is used as the thin film, the potential difference is 20 volts. An electric field applied to the thin film in this case is 2 volts per nanometer. This electric field is larger than a dielectric breakdown voltage of 1 volt per nanometer of the SiN thin film, and hence the thin film 100 is broken.

The condition under which a pore is formed in the thin film 100 due to dielectric breakdown varies depending on the device capacitance C of the thin film device as described above. Besides this, the condition varies also depending on a thickness t [nanometer] of the thin film 100, a dielectric breakdown voltage E [volt per nanometer] of the thin film 100, an area S [square meter] of the solution tanks 101 and 102 in which the static electricity 10 is generated, and a charge density difference $\Delta\sigma$ [charge per square meter] of the static electricity 10. An allowable charge density difference $\Delta\sigma$ [charge per square meter] of the static electricity 10 is represented by the following expression.

$$\Delta\sigma=(E \times t \times C)/S \quad (1)$$

Figure 7:
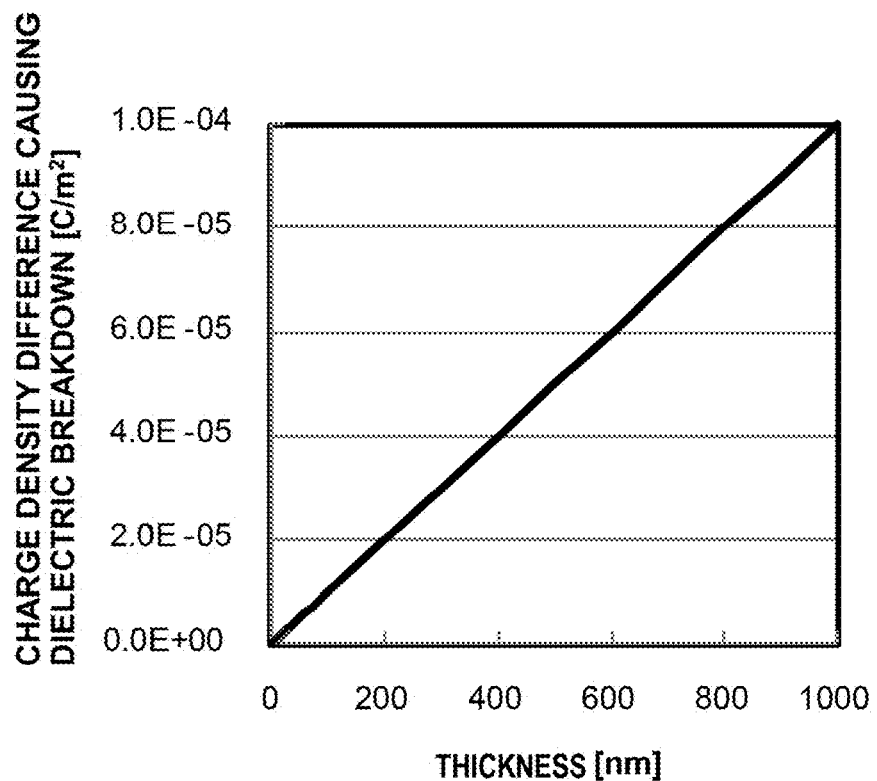
FIG. 7 is a graph for showing a relationship between the charge density difference of the static electricity and the thickness of the thin film.

FIG. 7 is a graph for showing a relationship between the charge density difference $\Delta\sigma$ of the static electricity 10 and the thickness t of the thin film 100. The horizontal axis represents the thickness t, and the vertical axis represents the charge density difference $\Delta\sigma$. In FIG. 7, as an example, it is assumed that the dielectric breakdown voltage E is 1 volt per nanometer, the area S of the solution tanks 101 and 102 in which the static electricity 10 is generated is 1 square centimeter, and the device capacitance C is 10 picofarads.

The charge density that may occur on a surface of an insulator is up to $\pm 5 \times 10^{-5}$ charge per square meter, and hence, under the above-mentioned condition, dielectric breakdown may occur due to the static electricity 10 in the thin film device having a thickness of 1 micrometer or less. Thus, through use of the expression (1), the allowable charge density difference $\Delta\sigma$ of the static electricity 10 can be roughly estimated, and the presence or absence of necessity of the countermeasures against static electricity can be determined.

Figure 8:
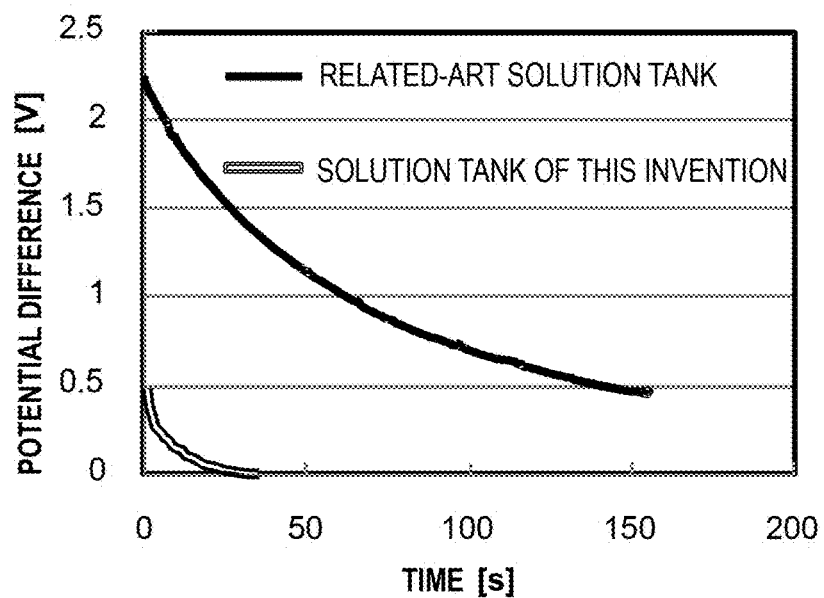
FIG. 8 is a graph for showing a change in potential difference at a time when static electricity is applied to the solution tank.

FIG. 8 is a graph for showing a change in potential difference at a time when static electricity is applied to the solution tank. The solution tank device having an antistatic mechanism according to the first embodiment decreases the potential difference generated between the solutions 103 and 104. In FIG. 8, there is shown a change with the passage of time in potential difference after the static electricity 10 is applied to an outside of the solution tank 101 in the same manner as in FIG. 5. A potential difference at a time of 0 seconds corresponds to the potential difference immediately after the static electricity 10 is applied. As is understood from FIG. 8, the potential difference can be decreased by the solution tank device having the antistatic mechanism according to the first embodiment.

In the experiment conducted here, an antistatic film is thinly applied to a part of an outside of the solution tank 101. In this case, the coating film peels off by the application of the static electricity 10, and static electricity is generated in a portion to which the antistatic film is not applied. The foregoing is considered to be the reason that an initial potential difference (potential difference immediately after the static electricity 10 is applied) cannot be decreased to 0 volts. Therefore, it is expected that the potential difference generated in the solution tank 101 in FIG. 8 is further decreased by increasing the thickness of the coating film and enlarging the coating area.

Example of Solution Tank Device Having Antistatic Mechanism

Next, the solution tank device having the antistatic mechanism to be used in the first embodiment is described with reference to FIG. 9 to FIG. 16. The solution tank device has a structure in which the thin film 100 is interposed between the insulating solution tanks 101 and 102. The solution tank device has a conductive structure configured to reduce the static electricity 10 generated by contact friction with at least an object outside of the solution tanks 101 and 102.

Figure 9:
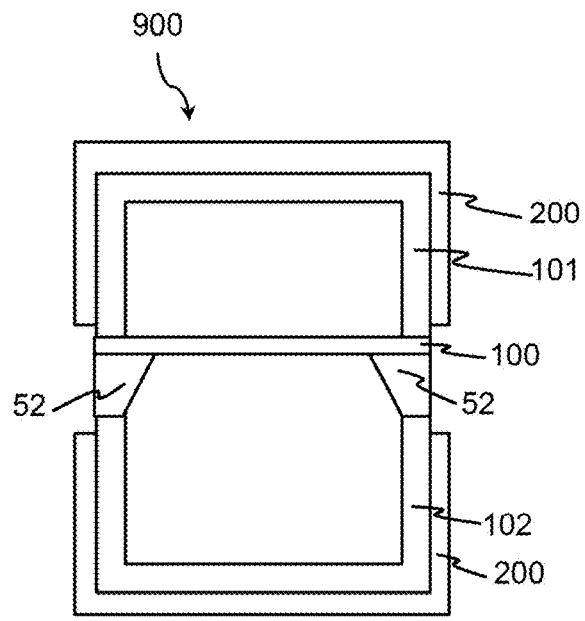
FIG. 9 is a sectional view of a first example of the solution tank device having an antistatic mechanism according to the first embodiment.

FIG. 9 is a sectional view of a first example of the solution tank device having an antistatic mechanism according to the first embodiment. A solution tank device 900 illustrated in FIG. 9 includes a conductive structure 200 on each outer side of the insulating solution tanks 101 and 102. The insulating solution tanks 101 and 102 are each made of, for example, an acrylic resin having a sheet resistance of $10^{14}$ ohms or more. The solution tanks 101 and 102 support the thin film device. The thin film device includes the thin film 100 and the support substrate 52. The thin film 100 may be subjected to dielectric breakdown through a gas, a liquid, and a solid in the solution tanks 101 and 102 due to the electric field given by the static electricity 10 generated outside of the insulating solution tanks 101 and 102. It is only required that the conductive structure 200 arranged on each of the solution tanks 101 and 102 have, for example, a sheet resistance of $10^{13}$ ohms or less, and may be made of a metal.

The conductive structure 200 may be, for example, a coating film obtained by applying a surfactant to each surface of the insulating solution tanks 101 and 102. Alternatively, the hydrophobic solution tanks 101 and 102 may be adopted. With this, water is adsorbed to the surfaces of the solution tanks 101 and 102 to enhance conductivity. Further, the conductive structure 200 may have a structure, for example, in which a conductive material is bonded to each of the surfaces of the insulating solution tanks 101 and 102. With this, the conductive structure 200 can be prevented from peeling off by friction that repeatedly occurs. Further, the conductive structure 200 may have a structure, for example, in which a metal thin film is formed on each of the surfaces of the insulating solution tanks 101 and 102 by vacuum deposition so that the surfaces are covered with a metal having high conductivity. With this, the static electricity 10 can be effectively leaked.

Figure 10:
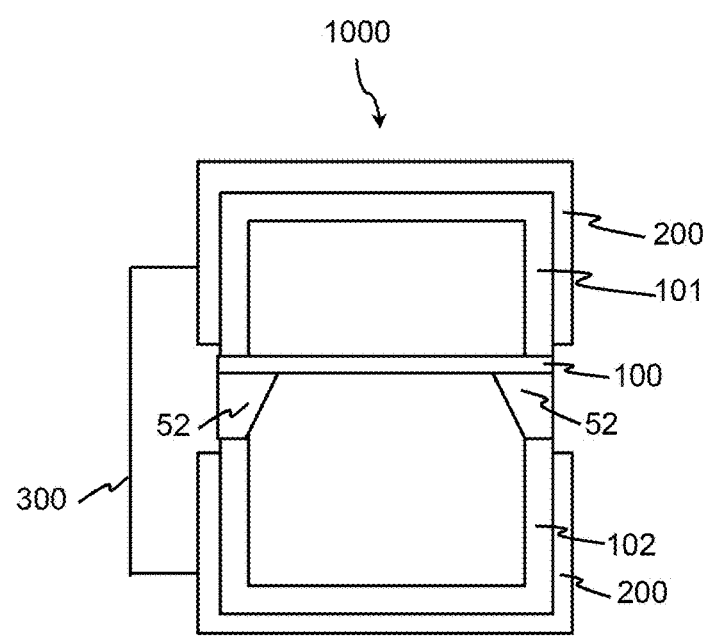
FIG. 10 is a sectional view of a second example of the solution tank device having an antistatic mechanism according to the first embodiment.

FIG. 10 is a sectional view of a second example of the solution tank device having an antistatic mechanism according to the first embodiment. A solution tank device 1000 of the second example illustrated in FIG. 10 has a structure in which the conductive structure 200 on an upper side of the solution tank device 900 of the first example illustrated in FIG. 9 and the conductive structure 200 on a lower side thereof are coupled to each other through wiring to be short-circuited. With this, the surfaces of the solution tanks 101 and 102 are set to an equipotential state, and the charge difference caused by the static electricity 10 can be further decreased.

Figure 11:
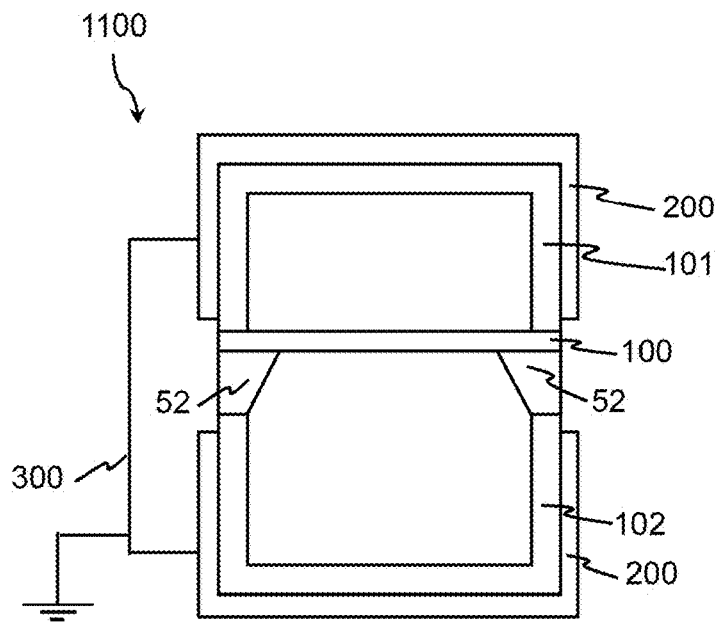
FIG. 11 is a sectional view of a third example of the solution tank device having an antistatic mechanism according to the first embodiment.

FIG. 11 is a sectional view of a third example of the solution tank device having an antistatic mechanism according to the first embodiment. A solution tank device 1100 of the third example illustrated in FIG. 11 has a structure in which wiring 300 of the solution tank device 1000 of the second example illustrated in FIG. 10 is grounded. With this, the static electricity 10 generated in the conductive structure 1100 can be leaked to outside through the wiring 300.

Figure 12:
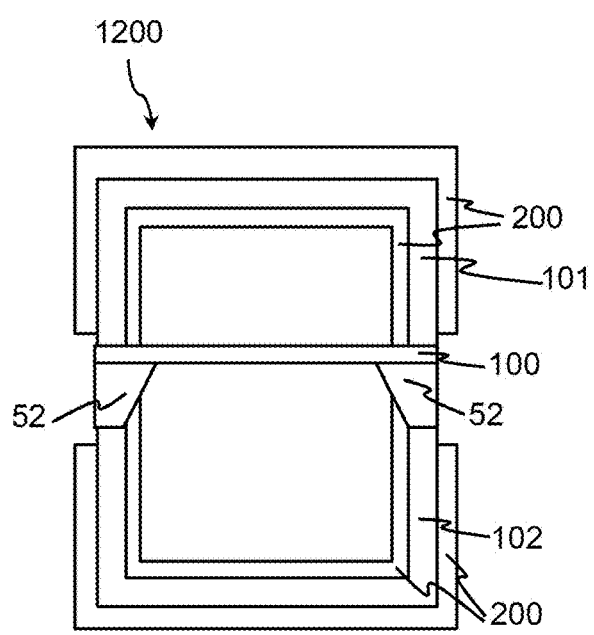
FIG. 12 is a sectional view of a fourth example of the solution tank device having an antistatic mechanism according to the first embodiment.

FIG. 12 is a sectional view of a fourth example of the solution tank device having an antistatic mechanism according to the first embodiment. A solution tank device 1200 of the fourth example illustrated in FIG. 12 has a structure in which the conductive structure 200 is arranged also on each inner side of the solution tanks 101 and 102. Even on the inner sides of the solution tanks 101 and 102, the static electricity 10 is generated. The generation of the static electricity 10 can be further suppressed by arranging the conductive structure 200 also on each of the inner sides of the solution tanks 101 and 102.

Figure 13:
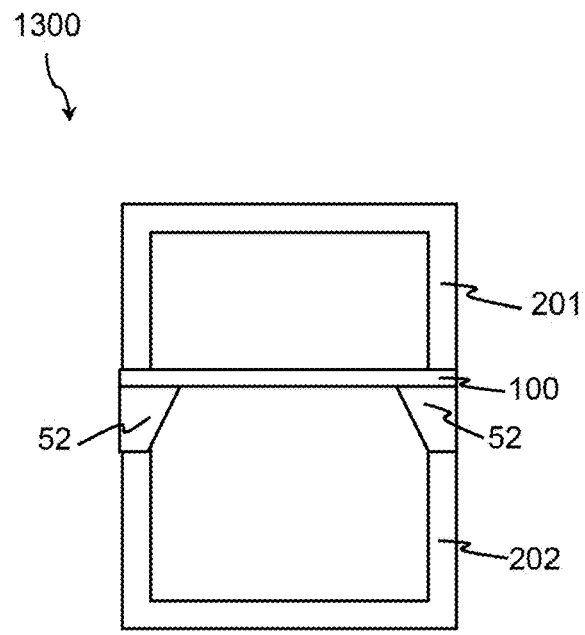
FIG. 13 is a sectional view of a fifth example of the solution tank device having an antistatic mechanism according to the first embodiment.

FIG. 13 is a sectional view of a fifth example of the solution tank device having an antistatic mechanism according to the first embodiment. A solution tank device 1300 of the fifth example illustrated in FIG. 13 has a structure using conductive solution tanks 201 and 202. In other words, the entire solution tank device 1300 is formed of a conductive material. The above-mentioned structure is useful when it is a difficult process or an expensive process to form a coating film or form a double-layer structure of a conductive material and an insulating material.

When a current passing through the thin film 100 is measured, in the solution tank devices 1200 and 1300 of the fourth and fifth examples, an interface between the solution and the inner side of the solution tank becomes conductive and noise may occur. Therefore, in the solution tank devices 1200 and 1300 of the fourth and fifth examples, an insulating material may be used at the interface between each of the solutions 103 and 104 and each of the inner sides of the solution tanks as in the solution tank device 900 of the first example.

Now, configurations common to the solution tank devices 900 to 1300 of the first to fifth examples are described. The thin film device may have a configuration, for example, in which the SiN thin film 100 having a thickness of 1 micrometer and an area of 100 square micrometers or less is supported by the silicon support substrate 52 having a thickness of 725 micrometers. When the thin film device is used as a nanopore sequencer device, $SiO_2$ may be used for the support substrate 52 supporting the thin film 100 having an insulating film applied thereto. Thus, noise of a high-frequency component can be reduced by decreasing the device capacitance.

Further, as shown in FIG. 2, in order to sufficiently reduce a noise current, it is desired that the insulating film be formed on the thin film device so as to have a device capacitance of 100 picofarads or less. Further, even in the thin film device in which the device capacitance is not decreased, when the dielectric breakdown voltage of the thin film device is small or when the initial charge difference $\Delta Q$ that occurs between the upper and lower solutions is large, there is a risk in that the potential difference $\Delta V(=\Delta Q/C)$ that occurs in the thin film 100 becomes larger than the dielectric breakdown voltage to cause the initial defect in the thin film 100. Therefore, even in the device in which the device capacitance is not decreased, prevention of occurrence of static electricity by the solution tank devices 900 to 1300 of the first to fifth examples is effective.

When the thin film device is used for measuring a sealing current, it is required that the thickness of the thin film 100 be selected appropriately in accordance with the size of an object to be measured. For example, when the object to be measured has a size of about 1 micrometer, it is preferred that the thin film 100 have a thickness of about 1 micrometer. Meanwhile, when a biological polymer having a width or a length of 20 nanometer or less is measured as the object to be measured, it is required to use the thin film 100 having a thickness of 20 nanometer or less in order to enhance the resolution as a sensor. In this case, as shown in FIG. 7, as the thickness t becomes smaller, the charge density difference $\Delta\sigma$ causing dielectric breakdown also becomes smaller, and hence the occurrence rate of the initial defect caused by the static electricity 10 increases. Therefore, the generation of the static electricity 10 can be effectively suppressed by mounting the thin film device including the thin film 100 having a thickness of 20 nanometers or less on the solution tank devices 900 to 1300 of the first to fifth examples.

Further, the thin film 100 having a pore with a diameter of 10 nanometers or less may be used. When the thin film 100 has the pore, a biological polymer, for example, DNA is caused to pass through the pore to measure a sealing current. In this case, when both the surface sides of the thin film 100 are filled with an electrolytic solution, in spite of the fact that the thin film 100 has the pore, a solution resistance occurring in the pore portion is large in a case where the pore diameter is small. Therefore, a potential difference of 0.01 volt per nanometer or more may occur in the thin film 100. Even when the thin film 100 has the pore in advance as described above, defects such as formation of a plurality of pores in the thin film 100 and enlargement of the pore formed in advance are caused through application of a potential difference of 0.01 volt per nanometer or more for a time period of 1 second or more. Therefore, it is required to prevent the static electricity 10.

Further, the thin film 100 may not have a pore. For example, in the case of using a procedure involving filling the thin film 100 with the solutions 103 and 104, and then applying a voltage to the thin film 100, to thereby open a pore having a diameter of 10 nanometers or less in the thin film 100 with satisfactory control, the pore is not opened at a time when the thin film 100 is incorporated into the solution tanks 101 and 102. When the pore is not opened, a larger potential difference is liable to be applied to the thin film 100, and an uncontrollable pore may be opened in the thin film 100. Therefore, it is effective to prevent occurrence of the static electricity 10 while the pore is not opened. Further, as a material for the thin film 100, an inorganic material such as SiN or graphene may be used so as to perform solid nanopore sequencing, or an organic material, for example, bionanopore in which protein nanopore is embedded in a lipid bilayer membrane may be used so as to perform bionanopore sequencing.

Figure 14:
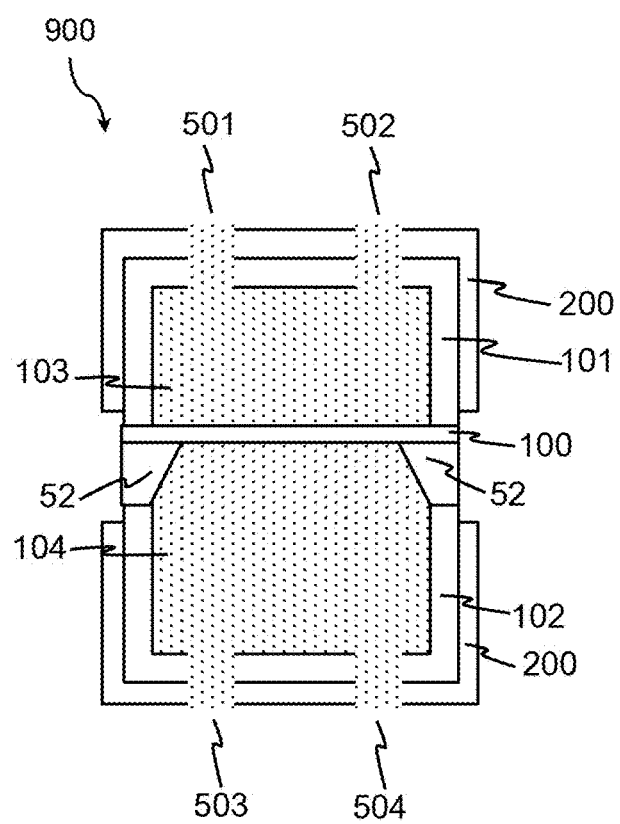
FIG. 14 is a sectional view for illustrating a state in which the solutions are filled in the solution tank device of the first example illustrated in FIG. 9.

FIG. 14 is a sectional view for illustrating a state in which the solutions 103 and 104 are filled in the solution tank device 900 of the first example illustrated in FIG. 9. Through filling of the solutions 103 and 104 in the solution tanks 101 and 102, a nanopore sensor capable of measuring an ion current passing through the thin film 100 is obtained in the solution tanks 101 and 102. Further, introduction ports 501 and 503 and discharge ports 502 and 504 may be formed so as to easily fill the solutions 103 and 104 in the solution tanks 101 and 102. For example, a distal end of each pipette is inserted in the introduction ports 501 and 503, and the solutions 103 and 104 are caused to flow in the solution tanks 101 and 102 from each pipette.

Further, an O-ring for preventing liquid leakage may be inserted between the thin film 100 and the solution tank 101 and between the thin film 100 and the solution tank 102. A small solution resistance in the solution tank leads to reduction in noise current. Therefore, it is desired that each passage length of the introduction ports 501 and 503 and the discharge ports 502 and 504 be set to 50 millimeters or less, and it is desired that each passage diameter of the introduction ports 501 and 503 and the discharge ports 502 and 504 be set to 1 millimeter or more. The solution tank device 900 of the first example is described in FIG. 14, but the foregoing is also applied to the solution tank devices 1000 to 1300 of the second to fifth examples.

Figure 15:
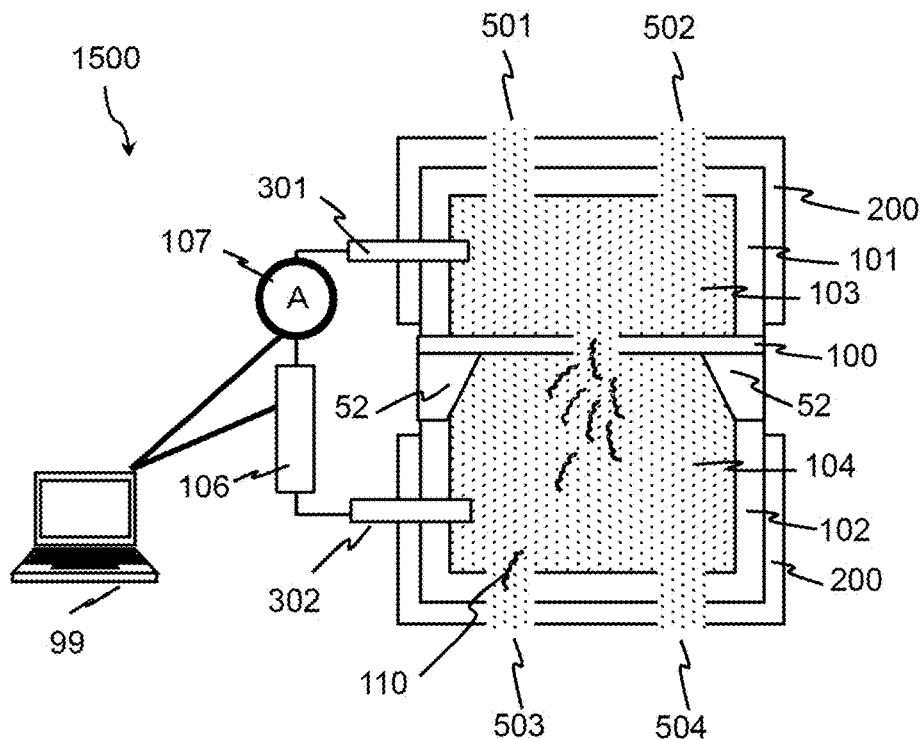
FIG. 15 is an explanatory view for illustrating an example of a nanopore sequencer.

FIG. 15 is an explanatory view for illustrating an example of a nanopore sequencer. A nanopore sequencer 1500 illustrated in FIG. 15 is a measurement system configured to measure a current passing through the thin film 100 with a computer 99 by coupling electrodes 301 and 302 to the solution tank device 900 of the first example filled with the solutions 103 and 104 illustrated in FIG. 14. In order to measure a current, the electrodes 301 and 302 are coupled to a power supply 106 and an ammeter 107. The computer 99 stores a sealing current value measured with the ammeter 107 in an internal storage device.

In this case, as an example, description is given of a case in which the solution tank 101 is coupled to the electrode 301, and the solution tank 102 is coupled to the electrode 302. Further, as the electrodes 301 and 302, for example, a Ag/AgCl electrode that has a simple structure and can be easily handled is used, and as the solutions 103 and 104, a 1 mol of KCl aqueous solution is used. Further, the solutions 103 and 104 contain, for example, DNA, protein, or nucleic acid as a biological polymer to be measured. The solutions 103 and 104 may also contain inorganic material particles as the object to be measured. In other words, it is only required that the object to be measured be a solution containing a substance that passes through a nanopore.

When the object to be measured is DNA, the nanopore sequencer 1500 can identify a base sequence forming the DNA based on a magnitude of a sealing current value at a time when the DNA passes through a nanopore. Further, when the object to be measured is a biological polymer or inorganic material particles other than the DNA, the nanopore sequencer 1500 can estimate the size of the object to be measured based on a magnitude of a sealing current value at a time when the biological polymer or the inorganic material particles pass through a nanopore.

Figure 16:
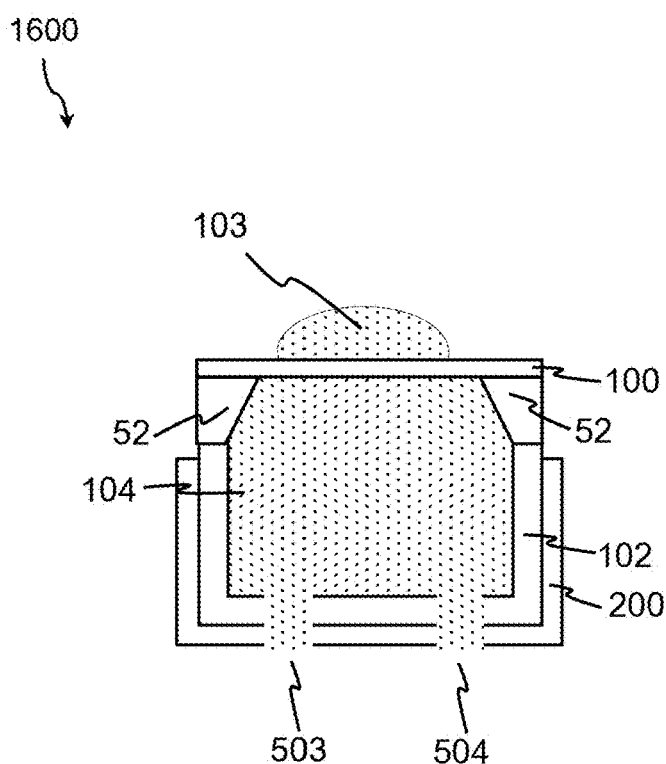
FIG. 16 is a sectional view for illustrating a sixth example of the solution tank device.

FIG. 16 is a sectional view for illustrating a sixth example of the solution tank device. A solution tank device 1600 of the sixth example has a structure in which the solution tank 101 of the solution tanks 101 and 102 in the solution tank device 900 illustrated in FIG. 9 is removed to leave the solution tank 102. Thus, the solution tank device may be asymmetric with respect to both surfaces of the thin film 100. There is no solution tank 101, and hence the solution 103 in a liquid droplet state is dropped to the surface of the thin film 100 with a pipette. With the solution tank device 1600 of the sixth example, the solution amount is reduced as compared to that of the solution tank device 900 of the first example, and hence a solution resistance is decreased. The solution tank device 1600 of the sixth example is described based on the solution tank device 900 of the first example in FIG. 16, but the solution tank 101 of the solution tanks 101 and 102 in the solution tank devices 1000 to 1300 of the second to fifth examples may be removed to leave the solution tank 102. Further, as illustrated in FIG. 15, a nanopore sequencer using the solution tank device 1600 of the sixth example may be constructed.

Second Embodiment

A second embodiment of this invention is a solution tank device in which the solution tank devices 900 to 1300 and 1600 of the first to sixth examples described in the first embodiment are arranged in an array pattern in a planar direction of the thin film 100. In the second embodiment, description is given of a solution tank device in which the solution tank devices 900 of the first example according to the first embodiment are arranged in an array pattern, but the solution tank devices of the second to sixth examples may be arranged in an array pattern. With this, the measurement speed of the object to be measured is increased.

Figure 17:
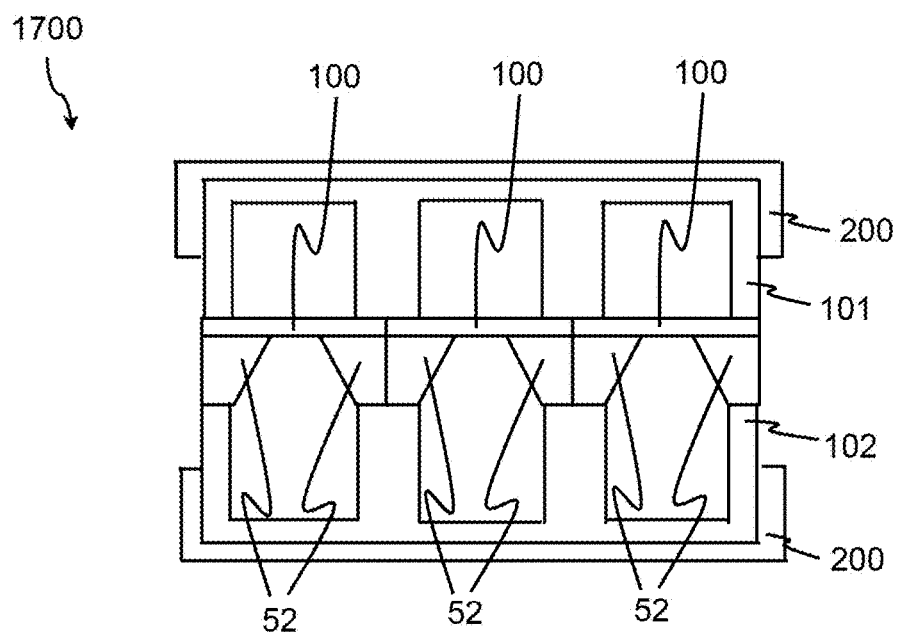
FIG. 17 is a sectional view for illustrating an example of the solution tank device according to the second embodiment.

FIG. 17 is a sectional view for illustrating an example of the solution tank device according to the second embodiment. In FIG. 17, there is illustrated a solution tank device 1700 in which the solution tank devices 900 of the first example according to the first embodiment are arranged in an array pattern. Also in the second embodiment, the solution tank device 1700 has the conductive structure 200. In the solution tanks 101 and 102, a partition wall is formed at an interface of each of the thin films 100, to thereby suppress inflow and outflow of the solution. With this, crosstalk noise between the solution tank devices of the array can be reduced.

Figure 18:
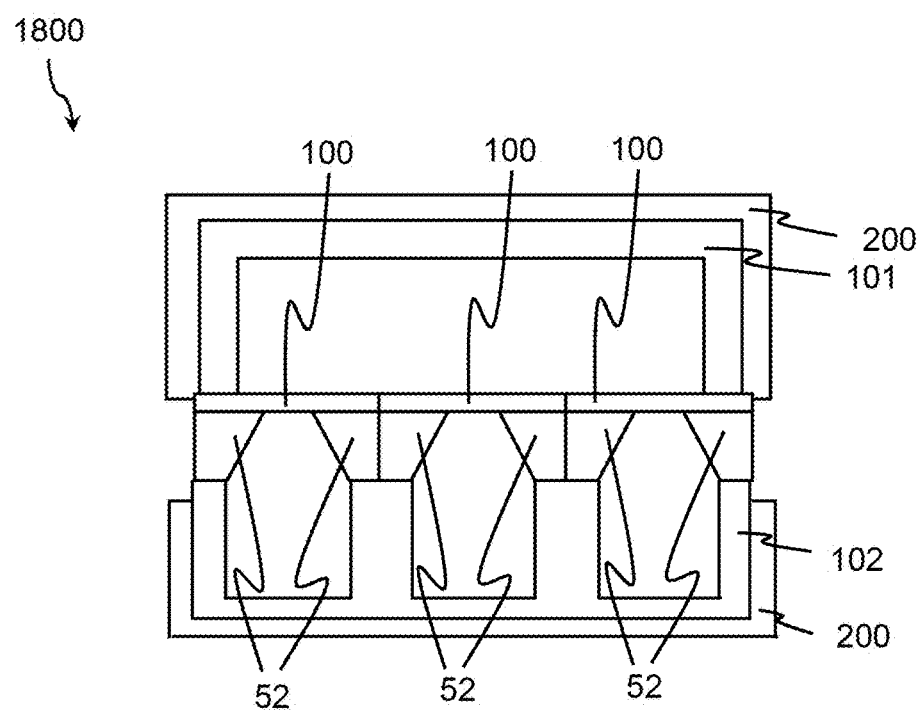
FIG. 18 is a sectional view for illustrating another example of the solution tank device according to the second embodiment.

FIG. 18 is a sectional view for illustrating another example of the solution tank device according to the second embodiment. A solution tank device 1800 of FIG. 18 is an example in which there is no partition wall on one surface side (solution tank 101 side in FIG. 18) of a plurality of thin films 100. In other words, the solution tanks 101 are coupled to each other between the solution tank devices of the array. When one surface side of each of the plurality of thin films 100 may be set to a common potential, the structure of FIG. 18 becomes simpler.

As described above, with the solution tank device according to the second embodiment, the initial defect of the thin film can be suppressed. Further, when the thin film is formed so as to allow a biological polymer to pass therethrough as the object to be measured, the solution tank device having the suppressed initial defect of the thin film can be used for measuring a biological polymer. Further, when the thin film is divided into a plurality of regions, the object to be measured is allowed to pass through the thin film for each region in parallel, and hence the measurement time can be shortened. Further, when the thickness of the thin film is set to 20 nanometers or less, the resolution as a sensor using the solution tank device can be enhanced in the case of measuring a biological polymer having a width or a length of 20 nanometers or less as the object to be measured.

Further, through use of the thin film having a thickness of 20 nanometers or less, generation of static electricity can be effectively suppressed. Further, when the thin film has a pore having a size of 10 nanometers or less, a biological polymer, for example, DNA is allowed to pass through the pore to measure a sealing current. Further, when a first solution is filled in a region surrounded by the solution tank and one surface of the thin film, a second solution is filled on the other surface of the thin film on an opposite side of the one surface, and any one of the first solution and the second solution contains the object to be measured, a sealing current of the object to be measured passing through the thin film can be measured by applying a potential difference to the first solution and the second solution with electrodes.

When the solution tank has an insulating structure having a seat resistance of $10^{14}$ ohms or more, and the solution is filled so as not to be brought into contact with a conductive structure, the conductive structure can be arranged in the solution tank. Further, when the conductive structure is arranged in the solution tank, generation of static electricity in the solution tank can be suppressed. Further, when the solution tank has the conductive structure, the solution tank device can have a simple configuration. When wiring for coupling conductive structures is formed, both the conductive structures can be set to an equipotential state to leak static electricity even when the static electricity is generated in the conductive structures.

It should be noted that this invention is not limited to the above-mentioned embodiments, and encompasses various modification examples and the equivalent configurations within the scope of the appended claims without departing from the gist of this invention. For example, the above-mentioned embodiments are described in detail for a better understanding of this invention, and this invention is not necessarily limited to what includes all the configurations that have been described. Further, a part of the configurations according to a given embodiment may be replaced by the configurations according to another embodiment. Further, the configurations according to another embodiment may be added to the configurations according to a given embodiment. Further, a part of the configurations according to each embodiment may be added to, deleted from, or replaced by another configuration.

What is claimed is:

1. A solution tank device, comprising:
   an insulating thin film, which is configured to allow an object to be measured to pass therethrough, and has a thickness of 1 micrometer or less;
   a first solution tank, which is configured to support one surface of both surfaces of the insulating thin film; and
   a first conductive structure, which has a sheet resistance of $10^{13}$ ohms or less in a portion in which contact friction occurs between the first solution tank and an object outside of the first solution tank.

2. The solution tank device according to claim 1, wherein the insulating thin film is configured to allow a biological polymer to pass therethrough as the object to be measured.

3. The solution tank device according to claim 2, wherein the insulating thin film is divided into a plurality of regions.

4. The solution tank device according to claim 1, wherein the insulating thin film has a thickness of 20 nanometers or less.

5. The solution tank device according to claim 1, wherein the insulating thin film has a pore having a diameter of 10 nanometers or less.

6. The solution tank device according to claim 1, further comprising:
   a first solution, which is filled in a region surrounded by the first solution tank and the one surface of the insulating thin film; and
   a second solution, which is filled on another surface of the insulating thin film on an opposite side of the one surface,
   wherein any one of the first solution and the second solution contains the object to be measured.

7. The solution tank device according to claim 6,
   wherein the first solution tank has an insulating structure having a sheet resistance of $10^{14}$ ohms or more, and
   wherein the first solution is filled so as to be inhibited from being brought into contact with the first conductive structure.

8. The solution tank device according to claim 7, further comprising a second conductive structure, which is arranged on an inner side of the first solution tank, and is brought into contact with the first solution.

9. The solution tank device according to claim 1, wherein the first solution tank comprises the first conductive structure.

10. The solution tank device according to claim 1, further comprising:
    a second solution tank, which is configured to support another surface of the insulating thin film; and
    a second conductive structure, which has a sheet resistance of $10^{13}$ ohms or less in a portion in which contact friction occurs between the second solution tank and an object outside of the second solution tank.

11. The solution tank device according to claim 10, further comprising wiring configured to set the first conductive structure and the second conductive structure to an equipotential state.

12. The solution tank device according to claim 10, further comprising:

a first solution, which is filled in a region surrounded by the first solution tank and the one surface of the insulating thin film; and a second solution, which is filled in a region surrounded by the second solution tank and the another surface of the insulating thin film, wherein any one of the first solution and the second solution contains the object to be measured.

13. The solution tank device according to claim 12, wherein the first solution tank has an insulating structure having a sheet resistance of $10^{14}$ ohms or more, wherein the first solution is filled so as to be inhibited from being brought into contact with the first conductive structure, wherein the second solution tank has an insulating structure having a sheet resistance of $10^{14}$ ohms or more, and wherein the second solution is filled so as to be inhibited from being brought into contact with the second conductive structure.

14. The solution tank device according to claim 13, further comprising a third conductive structure, which is arranged on an inner side of the first solution tank, and is brought into contact with the first solution.

15. The solution tank device according to claim 10, wherein the first solution tank comprises the first conductive structure, and wherein the second solution tank comprises the second conductive structure.

16. The solution tank device according to claim 1, wherein the first conductive structure is arranged on at least a side of the first solution tank.

* * * * *